United States Patent [19]

Klein et al.

[11] Patent Number: 4,820,810
[45] Date of Patent: Apr. 11, 1989

[54] UREA CATALYST FOR PREPARATION OF SUCROSE POLYOLS USEFUL FOR RIGID POLYURETHANE FOAMS

[75] Inventors: Howard P. Klein; Michael E. Brennan, both of Austin, Tex.

[73] Assignee: ARCO Chemical Technology, Inc., Wilmington, Del.

[21] Appl. No.: 924,660

[22] Filed: Oct. 30, 1986

[51] Int. Cl.$^4$ .................. C08G 18/14; C08G 65/26
[52] U.S. Cl. .................... 536/4.1; 536/18.3; 536/18.6; 521/115; 521/167
[58] Field of Search .............. 536/18.3, 18.6, 4.1

[56] References Cited

U.S. PATENT DOCUMENTS

| 3,085,085 | 4/1963 | Wismer et al. | 527/300 |
|---|---|---|---|
| 3,153,002 | 10/1964 | Wismer et al. | 521/120 |
| 3,763,111 | 10/1973 | Fijal | 528/85 |
| 4,230,824 | 10/1980 | Nodelman | 536/120 |
| 4,332,936 | 6/1982 | Nodelman | 536/120 |
| 4,380,502 | 4/1983 | Muller et al. | 536/18.3 |
| 4,446,313 | 5/1984 | Dix et al. | 536/18.6 |
| 4,459,397 | 7/1984 | Richardson et al. | 527/300 |
| 4,465,791 | 8/1984 | Klein et al. | 521/115 |
| 4,481,308 | 11/1984 | Gray | 521/120 |
| 4,485,032 | 11/1984 | Olstowski et al. | 560/158 |
| 4,499,264 | 2/1985 | McDaniel | 527/300 |
| 4,734,442 | 3/1988 | Viswanathan | 521/167 |

FOREIGN PATENT DOCUMENTS 212967 8/1984 German Democratic Rep. .

OTHER PUBLICATIONS

Le Maistre et al., "The Reaction of Sucrose with Ethylene Oxide," J. Org. Chem., 13, pp. 782–785 (1948).
Tousignant et al., "Reaction of Ethylene Oxide with Urea," J. Org. Chem. 22, pp. 166–167.

Primary Examiner—Ronald W. Griffin
Attorney, Agent, or Firm—Steve Rosenblatt; David L. Mossman

[57] ABSTRACT

Catalytic quantities of urea are used in the alkoxylation of aqueous sucrose to prepare low color polyols useful in rigid polyurethane foams.

20 Claims, No Drawings

UREA CATALYST FOR PREPARATION OF SUCROSE POLYOLS USEFUL FOR RIGID POLYURETHANE FOAMS

BACKGROUND OF THE INVENTION

1. Field of the Invention

This invention pertains to the alkoxylation of polyhydric initiators to prepare polyols useful in manufacturing rigid polyurethane foams. More particularly, the invention pertains to the use of catalytic quantities of urea for the alkoxylation of polyhydric initiators, in particular sucrose, and the rigid urethane foams made therefrom.

2. Description of the Related Art

It is known that crosslinking polyols which possess a high functionality, that is, a high number of free hydroxyl groups, can be used to produce polyurethane cellular products with good strength and dimensional stability. In general, the higher the functionality of the polyol used, the greater the rigidity of the polyurethane product. Thus, sucrose polyols having a functionality of 8 are of importance in rigid polyurethane foam preparation as disclosed, for example, in U.S. Pat. No. 3,763,111.

It is known to prepare sucrose polyols by reacting sucrose with alkylene oxide in an aqueous solution in the presence of sodium hydroxide. See, for example, LeMaistre, et al., *J. Org. Chem.*, 13, p 782, (1948). U.S. Pat. Nos. 3,085,085 and 3,153,002 disclose a process based on this reaction in which sucrose is reacted at elevated temperatures with ethylene oxide or propylene oxide in a concentrated aqueous solution in the presence of potassium hydroxide catalyst. Such processes, however, are subject to undesirable secondary reactions such as partial hydrolysis of the alkylene oxide by the water used as the reaction medium, resulting in a product which is very dark in color. In order to provide a method which prevents discoloring and the other problems associated with those processes, U.S. Pat. No. 4,380,502 to Muller, et al. discloses the use of polyether polyols made by alkoxylating a mixture which is from 20 to 80 wt.% sucrose and 80 to 20 wt.% formitol. Muller, et al. teach that the polyether polyols prepared according to their process exhibit a color ranging from clear to yellowish.

U.S. Pat. No. 4,230,824 to Nodelman discloses a method for preparing a sucrose based polyether polyol which involves the use of a polyalkylene polyamine as both co-initiator and catalyst for the alkoxylation reaction of sucrose. Nodelman reports, however, that the resulting polyols are very high in color; i.e., up to 12 Gardner. In a later patent, however, U.S. Pat. No. 4,332,936, Nodelman reports a method for making polyether polyols from sucrose comprising dissolving the sucrose in a solvent such as dimethylformamide in the presence of a co-initiator and amine catalyst prior to alkoxylation. Nodelman reports that this process enables the reaction to be conducted at temperatures as low as 80° C., producing a product with consistently low color; for example, a Gardner color in the 2 to 3 range.

Applicants have surprisingly found urea is an effective catalyst and co-initiator for the alkoxylation of aqueous sucrose solutions and results in polyol products which are much lower in color than prior art polyols; i.e., on the order of 1 Gardner.

Urea has been added to polyols for other purposes. U.S. Pat. No. 4,485,032 teaches that the addition of a minor amount of urea and/or substituted ureas to incompatible polyol blends often renders these mixtures compatible and produces a single phase liquid. Urea has also been added to polyols to prepare fire retardant polyurethane foams, as demonstrated in U.S. Pat. No. 4,481,308.

In order to avoid the mechanical difficulties encountered in mixing urea with polyurethane foams to produce a self-extinguishing foam, U.S. Pat. No. 4,459,397 to Richardson, et al. teaches that a polyether polyol exhibiting improved fire resisting qualities may be prepared by reacting a reducing sugar with propylene oxide to produce a polyether polyol which is then reacted with unsubstituted urea to chemically bind the urea thereto to produce a modified polyether polyol. Richardson, et al. also report, however, that attempts to react urea and a sucrose polyether polyol were unsuccessful.

DD 212,967 discloses polyether polyols useful in rigid polyurethane foams that are prepared by polymerizing a portion of the required amount of epoxide on urea or its derivatives and then adding polyoxypropylated glycerol-urea and KOH catalyst.

Tousignant, et al., in "Reaction of Ethylene Oxide with Urea," *J. Org. Chem.*, 22, pp 166-167, disclose that the reaction of urea with alkylene oxides produces alkoxylated ureas and amino carbamates.

SUMMARY OF THE INVENTION

The invention is a polyol prepared by the process comprising reacting a polyhydric initiator or mixtures thereof with one or more alkylene oxides in the presence of a catalytically effective amount of urea.

Although sucrose is the preferred polyhydric initiator and is referred to specifically below, also within the scope of this invention are other initiators known to those skilled in the art, such as as ethylene glycol, polyethylene glycol, propylene glycol, polypropylene glycol, glycerine, sorbitol, trimethylolpropane, alphamethylglucoside and pentaerythritol. Therefore, it is within the scope of this invention to use any of these initiators alone or in mixtures. Those skilled in the art will readily recognize any minor differences and will be able to make appropriate adjustments for any initiator.

DETAILED DESCRIPTION OF THE PREFERRED EMBODIMENTS

Conventional sucrose polyols are prepared by reacting sucrose with alkylene oxides containing 2 to 4 carbon atoms, or mixtures thereof, usually in a mole ratio of alkylene oxide to sucrose ranging from about 8:1 to about 20:1. The hydroxyl number which is desired for the finished polyol will determine the amount of alkylene oxide used to react with the sucrose. Generally, the polyol is prepared by reacting the sucrose with propylene oxide or ethylene oxide or by reacting the sucrose first with propylene oxide followed by ethylene oxide, or vice versa, in one or more sequences to give a so-called block polymer chain, or by reacting the sucrose with a mixture of propylene oxide and ethylene oxide to achieve a random distribution of such alkylene oxides. Useful polyols usually have a hydroxyl number ranging from about 200 to about 800, preferably between 300 and 700, and more preferably between about 400 and about 600. The method of reacting sucrose with alkylene oxides is well known and is described in U.S. Pat. No. 3,153,002. Briefly, the method consists essentially of dissolving the sucrose in a small amount of water, for example from about 5% to about 20%, in a pressure container, and contacting the resultant solution with the alkylene oxide under pressure until a desired degree of oxyalkylation has been obtained.

Typically, the reaction would be catalyzed with a base such as sodium hydroxide, sodium carbonate, sodium acetate or trimethylamine, the amount thereof being within the range of about 0.1% to about 10%. However, in the practice of this invention, urea serves as both catalyst and as a co-initiator in the alkoxylation reaction. Preferably, the mole ratio of urea to sucrose is in the range of about 0.1:1 to about 10:1. It is especially preferred that the mole ratio of urea to sucrose is from about 0.2:1 to about 2:1.

Tertiary amine co-catalysts may also be present. Examples of suitable tertiary amines include N-alkylmorpholines, N,N-dialkylalkanolamines, N,N-dialkylcyclohexylamines and alkyl amines where the alkyl groups are methyl, ethyl, propyl, butyl, etc. Examples of specific tertiary amine catalysts useful in the invention are triethylenediamine, tetramethylethylenediamine, triethylamine, tripropylamine, tributylamine, triamylamine, pyridine, quinoline, dimethylpiperazine, dimethylhexahydroaniline, dimethylpiperazine, N-ethylmorpholine, dimethylaniline, nicotine, tetramethylpropanediamine and methyl triethylenediamine. Especially preferred are triethanolamine and THANCAT® DME, tradename for N,N-dimethylaminoethanol.

The alkoxylation of aqueous sucrose should preferably be conducted at a temperature range of 60° to 130° C. and a pressure of 1 atmosphere to 200 psig. Especially preferred are a temperature range of 80° to 110° C. and a pressure of 40 to 60 psig.

Manufacture of Rigid Polyurethane Foam

The components utilized for the manufacture of a rigid polyurethane foam include a polyol, an organic polyisocyanate, a blowing agent, a surfactant, a catalyst, suitable fire retardants and other additives. Typical aromatic polyisocyanates which may be reacted with the polyols of the instant invention include m-phenylene diisocyanate, p-phenylene diisocyanate, polymethylene polyphenylisocyanate, 2,4-toluene diisocyanate, 2,6-tolylene diisocyanate, dianisidine diisocyanate, bitolylene diisocyanate, naphthalene-1,4-diisocyanate, diphenylene-4,4'-diisocyanate and aliphatic-aromatic diisocyanates such as xylylene-1,4-diisocyanate, xylylene-1,2-diisocyanate, xylylene-1,3-diisocyanate, bis(4-isocyanatophenyl)methane, bis(3-methyl-4-isocyanatophenyl)methane, and 4,4'-diphenylpropane diisocyanate.

Preferred aromatic polyisocyanates used in the practice of the invention are methylene-bridged polyphenyl polyisocyanate mixtures which have a functionality of from about 2 to about 4. These latter isocyanate compounds are generally produced by the phosgenation of corresponding methylene bridged polyphenyl polyamines, which are conventionally produced by the reaction of formaldehyde and primary aromatic amines, such as aniline, in the presence of hydrochloric acid and/or other acidic catalysts. Known processes for preparing the methylene-bridged polyphenyl polyamines and corresponding methylene-bridged polyphenyl polyisocyanates therefrom are described in the literature and in many patents; see for example, U.S. Pat. Nos. 2,683,730; 2,950,263; 3,012,008; 3,344,162; and 3,362,979.

The more preferred methylene-bridged polyphenyl polyisocyanate mixtures used here contain from about 20 to about 100 weight percent methylene diphenyl diisocyanate isomers with the remainder being polymethylene polyphenyl polyisocyanates having higher functionalities and higher molecular weights. Typical of these are polyphenyl polyisocyanate mixtures containing about 20 to 100 weight percent methylene diphenyl diisocyanate isomers, of which 20 to about 95 weight percent thereof is the 4,4'-isomer, with the remainder being polymethylene polyphenyl polyisocyanates of higher molecular weight and that have an average functionality of from about 2.1 to about 3.5. The isocyanate mixtures are known materials and can be prepared, for example, by the process described in U.S. Pat. No. 3,362,979.

In the production of rigid polyurethane foams in the practice of the invention, other known additives are necessary. One such constituent is the blowing agent. Some examples of such material are trichloromonofluoromethane, dichlorodifluoromethane, dichloromonofluoromethane, 1,1-dichloro-1-fluoroethane, 1,1-difluoro-1,2,2-trichloroethane, chloropentafluoroethane, and the like. Other useful blowing agents include low-boiling hydrocarbons such as butane, pentane, hexane, cyclohexane, and the like. See U.S. Pat. No. 3,072,582, for example.

The catalysts which may be used to make the foams are well known. There are two general types of useful catalysts: tertiary amines and organometallic compounds. Suitable tertiary amines include those discussed earlier as useful co-catalysts for the alkoxylation of sucrose.

Organometallic compounds useful as catalysts include those of bismuth, lead, tin, titanium, iron, antimony, uranium, cadmium, cobalt, thorium, aluminum, mercury, zinc, nickel, cerium, molybdenum, vanadium, copper, manganese, zirconium, etc. Some examples of these metal catalysts include bismuth nitrate, lead 2-ethylhexoate, lead benzoate, lead oleate, dibutyltin dilaurate, tributyltin, butyltin trichloride, stannic chloride, stannous octoate, stannous oleate, dibutyltin di(2-ethylhexoate), ferric chloride, antimony trichloride, antimony glycolate, tin glycolates, etc. Selection of the individual catalysts and proportions to use in the polyurethane reaction are well within the knowledge of those skilled in the art, and an amine and organometallic compound are often used together in the polyurethane reaction.

Conventional formulation ingredients are also employed such as, for example, foam stabilizers, also known as silicone oils or emulsifiers. The foam stabilizer may be an organic silane or siloxane. For example, compounds may be used having the formula:

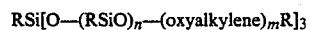

wherein R is an alkyl group containing from 1 to 4 carbon atoms, n is an integer of from 4 to 8, m is an integer of 20 to 40, and the oxyalkylene groups are derived from propylene oxide and ethylene oxide. See, for example, U.S. Pat. No. 3,194,773.

The flame retardancy of the polyurethane composition can be enhanced by using known fire retardants. Examples of suitable flame retardants are: tris(1,3-dichloropropyl)phosphate, tris(2,3-dibromopropyl)- phosphate, 2,2-bis(chloromethyl)-1,3 propylene bis[-di(2-chloroethyl)phosphate], tris(2-chloroethyl)phosphate, tris(2-chloropropyl)phosphate, bis(dichloropropyl)tribromopentyl phosphate, tetrakis-(2-chloroethyl)ethylene diphosphate (sold by Olin Chemical as THERMOLIN® 101), oligomeric chloroalkyl phosphate (sold by Stauffer Chemical Co. as FYROL® EFF), tricresyl phosphate, cresyl diphenyl phosphate, chlorinated paraffins and brominated paraffins. Halogenated phosphates are preferred flame retardants in the practice of this invention, such as tris(1,3-dichloropropyl)phosphate, tris(2-chloroethyl)phosphate, chloroalkyl phosphate and tetrakis(2-chloroethyl)ethylene diphosphate. Although a single flame retardant is preferred from the standpoint of simplicity of formulation, mixtures of two or more of the same type or of different types may be found to give improved performance in some cases, and such mixtures are included in the scope of this invention. The amount of flame retardant can be varied over a wide range of from about 20 to about 60 parts by weight per 100 parts of weight of polyol in the reaction mixture. It is preferred to use from about 20 to about 40 parts by weight.

The rigid polyurethane foams can be made in one step by reacting all the ingredients together at once (one-shot process). The rigid foams can also be made by the so-called "quasi-prepolymer method" wherein a portion of the polyol component is reacted in the absence of a catalyst with the polyisocyanate component in proportion so as to provide from about 20 percent to about 40 percent to free isocyanato groups in the reaction product, based on the polyol. To prepare foam, the remaining portion of the polyol is added and the two components are allowed to react in the presence of a catalyst and other appropriate additives such as blowing agents, foam stabilizing agents, fire retardants, etc. The blowing agent, the foam stabilizing agent, the fire retardant, etc., may be added to either the prepolymer or remaining polyol, or both, prior to the mixing of the component, whereby at the end of the reaction a rigid polyurethane foam is provided. The invention will be further illustrated by the following non-limiting examples.

EXAMPLE 1

Deionized water, solid sucrose, urea and, in some examples, a tertiary aminoalkanol co-catalyst was charged to a clean and dry nitrogen purged 5-15 gallon jacketed, stirred kettle. The whole was then stirred and heated to 80° C. and held for one hour. Alkylene oxide No. 1, generally oxide (EO) but in several cases propylene oxide (PO), was then added at 50 psig maximum over a period of 2-3 hours followed by a one to two hour digestion period. Water was then partially removed overhead at 80° C. under vacuum such that the water level of the kettle contents was reduced to 8-10% (2.6-3.2 lbs water removed). The whole was then heated to 110° C. and then alkylene oxide No. 2, generally PO but in one case mixed oxide (10:90 wt.% EO/PO), was added at 50 psig max. over a period of 2-8 hours (usually 2-4 hours) followed by a 2 hour digestion period. The kettle was then vented and the kettle contents purged with nitrogen (30 minutes), sampled (% water, 1-3%) and stripped of volatiles at 110° C. under vacuum. The product was then isolated warm. Table I details reaction charges, yields and product analyses.

Foams were prepared from several inventive polyols and several commercially available sucrose-based polyols; i.e. VORANOL® 360 and 370 (Dow), MULTRANOL® 4034 (Mobay) and NIAX® FAF-529 (Union Carbide). The inventive polyols used were those prepared according to Examples 7 and 8 of Table I. The formulation components were mixed at 2700 rpm and poured into an 8"×8"×12" (600 g pours) open mold and allowed to rise. The resulting foams were allowed to stand at room temperature for three days before testing. Formulations, reaction profiles and foam physical properties are found in Table II.

TABLE I

| Ex. | D.I. Water | Sucrose | Urea | Co-Cat. | Ethylene Oxide | Propylene Oxide | 10/90 wt. % EO/PO | Cycle Time, Hours | Product Yield, % | Hydroxyl No. | Visc. 25° C., cps | Total Amine Meq/g | Water, % | Gardner Color |
|---|---|---|---|---|---|---|---|---|---|---|---|---|---|---|
| 1[a] | 4.95 | 10.05 (1.0) | 0.72 (0.41) | — | 7.76 (5.99) | 17.96 (10.52) | — | 20.8 | 97.0 | 541 | 6840 | 0.15 | 0.01 | <1 |
| 2 | 4.95 | 10.05 (1.0) | 0.72 (0.41) | — | 7.76 (5.99) | 18.02 (10.55) | — | 15.8 | 91.0 | 557 | 9880 | 0.17 | 0.01 | 1 |
| 3 | 4.95 | 10.05 (1.0) | 0.72 (0.41) | — | 7.76 (5.99) | 19.39 (11.35) | — | 13.0 | 94.8 | 542 | 9030 | 0.15 | 0.09 | 1 |
| 4 | 4.95 | 10.05 (1.0) | 0.72 (0.41) | — | 7.76 (5.99) | 20.88 (12.23) | — | 12.0 | 94.5 | 535 | 6820 | 0.17 | 0.02 | 1 |
| 5 | 4.95 | 10.05 (1.0) | 2.17 (1.23) | 0.20[b] (0.04) | 6.38 (4.93) | 23.61 (13.83) | — | 11.7 | 99.6 | 573 | 7530 | 0.45 | 0.03 | 1 |
| 6 | 4.95 | 10.05 (1.0) | 2.17 (1.23) | 0.20[b] (0.04) | — | 8.41; 21.58 (4.93) (12.64) | — | 19.3 | 86.6 | 756 | 8660 | 0.82 | 0.03 | 1 |
| 7 | 4.95 | 10.05 (1.0) | 1.44 (0.82) | — | 7.76 (5.99) | 23.16 (13.56) | — | 13.4 | 98.5 | 520 | 5550 | 0.23 | 0.03 | 1 |
| 8 | 4.95 | 10.05 (1.0) | 1.44 (0.82) | — | 7.76 (5.99) | — | 23.16 (13.99) | 11.8 | 98.9 | 498 | 4990 | 0.20 | 0.01 | <2 |
| 9 | 4.93 | 10.00 (1.0) | 0.72 (0.41) | 0.12[c] (0.04) | — | 10.18; 21.17 (6.00) (12.48) | — | 14.2 | 94.0 | 584 | 8920 | 0.22 | 0.01 | — |
| 10 | 4.93 | 10.00 (1.0) | 1.44 (0.82) | 0.12[c] (0.04) | — | 10.18; 20.45 (6.00) (12.06) | — | 14.3 | 93.6 | 615 | 9880 | 0.31 | 0.01 | — |

[a]Urea was added in three portions in order to determine the minimum level required.
[b]Triethanolamine (TEA).
[c]THANCAT® DME.

TABLE II

|  | A | B | C | D | E | F |
|---|---|---|---|---|---|---|
| Formulation, pbw |  |  |  |  |  |  |
| Ex. 7 (OH = 520) | 37.3 | — | — | — | — | — |
| Ex. 8 (OH = 498) | — | 38.2 | — | — | — | — |
| V-360$^d$ (OH = 378) | — | — | 44.1 | — | — | — |
| V-370$^e$ (OH — 383) | — | — | — | 43.9 | — | — |
| M-4034$^f$ (OH = 497) | — | — | — | — | 38.3 | — |
| FAF-529$^g$ (OH = 530) | — | — | — | — | — | 36.9 |
| DC-193$^h$ | 0.5 | 0.5 | 0.5 | 0.5 | 0.5 | 0.5 |
| FREON R-11A$^i$ | 13.0 | 13.0 | 13.0 | 13.0 | 13.0 | 13.0 |
| THANCAT ® TD-33A$^j$ | 0.5 | 0.5 | 0.5 | 0.5 | 0.5 | 0.5 |
| RUBINATE ® M$^k$ (I = 1.05) | 48.7 | 47.8 | 41.9 | 42.1 | 47.7 | 49.1 |
| Reaction Profile |  |  |  |  |  |  |
| Times (sec), Mixing | 15 | 10 | 15 | 15 | 15 | 15 |
| Times (sec), Cream | 25 | 12 | 42 | 61 | 72 | 26 |
| Times (sec), Gel | 53 | 31 | 143 | 162 | 171 | 61 |
| Times (sec), Tack Free | 70 | 45 | 201 | 195 | 186 | 88 |
| Times (sec), Rise | 173 | 84 | 307 | 375 | 317 | 185 |
| Initial Surface Friability |  |  | None |  |  |  |
| Foam Appearance |  |  | Good |  |  |  |
| Physical Properties |  |  |  |  |  |  |
| Density, pcf | 2.14 | 2.21 | 2.32 | 2.50 | 2.20 | 2.16 |
| K-Factor | 0.118 | 0.108 | 0.125 | 0.135 | 0.130 | 0.112 |
| Compressive strength psi, |  |  |  |  |  |  |
| with rise | 37.31 | 38.68 | 41.05 | 44.14 | 35.85 | 43.35 |
| against rise | 16.26 | 15.32 | 14.08 | 15.83 | 19.46 | 16.22 |
| Heat distortion, °C. | 178 | 170 | 140 | 162 | 201 | 178 |
| % Closed cells | 86.89 | 89.88 | 91.72 | 91.68 | 86.61 | 94.27 |
| Friability (% wt. loss, 10 min) | 12.78 | 7.93 | 4.22 | 16.55 | 18.54 | 8.49 |
| Dimensional Stability |  |  |  |  |  |  |
| 158° F., 100% RH, 1 week, |  |  |  |  |  |  |
| ΔV | +5.4 | +7.5 | +20.2 | +8.1 | +5.2 | +5.3 |
| ΔW | −2.5 | −2.2 | −2.1 | −1.5 | −1.8 | −2.0 |
| ΔL | +2.8 | +4.2 | +11.9 | 5.2 | +3.0 | +3.2 |
| 158° F., 100% RH, 4 weeks |  |  |  |  |  |  |
| ΔV | +8.6 | +12.4 | +23.0 | +10.0 | +6.9 | +9.3 |
| ΔW | −3.8 | −3.5 | −4.3 | −3.8 | −3.3 | −2.5 |
| ΔL | +4.7 | +6.7 | +13.2 | +6.4 | +3.9 | +5.4 |

$^d$VORANOL ® 360 (Dow);
$^e$VORANOL ® 370 (Dow);
$^f$MULTRANOL ® 4034: (Mobay),
$^g$NIAX ® FAF-529 (Union Carbide);
$^h$Dow-Corning silicone;
$^i$DuPont FCCl$_3$;
$^j$Texaco Chemical Co. tertiary amine catalyst;
$^k$Rubicon polymeric isocyanate.

EXAMPLE 2

Table III details reaction charges, yields and product analyses for various sucrose-amino polyols. Note the color of those polyols prepared with urea as contrasted with the color of those prepared with the various amines used.

Table IV details formulations, reaction profiles and physical properties of foams prepared using several of the polyols found in Table III.

TABLE III

|  | Sucrose-Amino Polyols | | | | | | | | |
|---|---|---|---|---|---|---|---|---|---|
|  | A | B | C | D | E | F | G | H | I |
| Reactants |  |  |  |  |  |  |  |  |  |
| Sucrose (lbs) | 5.7 | 5.7 | 17.1 | 5.7 | 20.2 | 3.42 | 6.84 | 6.84 | 3.42 |
| Monoethanolamine (lbs) | 1.22 | — | 6.1 | — | — | — | — | — | — |
| Diethanolamine (lbs) | — | 2.0 | — | — | — | — | — | — | — |
| 1,2-Diaminocyclohexane (lbs) | — | — | — | 1.0 | — | 1.14 | — | — | — |
| Aminopropyldiethanolamine (lbs) | — | — | — | — | 5.16 | — | — | — | — |
| Urea (lbs) | — | — | — | — | — | — | 2.4 | 1.2 | 1.2 |
| Ethylene oxide (lbs) | 2.64 | 1.7$^1$ | 4.4 | 2.3 | 10.0 | 1.76 | 7.0 | 5.3 | 2.6 |
| EO/N—H (mole ratio) | 1.5 | 2.0 | 0.5 | 1.5 | 1.9 | 1.0 | 1.0 | 1.5 | 0.75 |
| Precursor water (wt. %) | 6.6 | 10.4 | 5.8 | 8.9 | 6.7 | 10.0 | 8.5 | 9.8 | 8.0 |
| Propylene oxide (lbs) | 15.0 | 15.0 | 58.0$^2$ | 15.0 | 35.0 | 7.54 | 20.0 | 15.0 | 9.3 |
| PO/EO (mole ratio) | 4.3 | 6.7 | 10.0 | 4.9 | 2.6 | 3.25 | 2.8 | 2.15 | 2.7 |
| Final water prior to stripping (wt. %) | 2.6 | 2.6 | 1.8 | 1.9 | 2.6 | 3.0 | 2.0 | — | 2.2 |
| Reaction conditions |  |  |  |  |  |  |  |  |  |
| Precursor preparation time (hrs)/°C. | 3.0/80 | 2.0/80 | 2.5/80 | 2.0/80 | 2.0/80 | 2.0/80 | 1.5/80 | 1.5/80 | 1.5/80 |
| PO addition time (hrs)/°C. | 1.0/110 | 2.0/110$^1$ | 2.0/110 | 1.5/110 | 2.0/110 | 2.0/110 | 1.5/110 | 1.0/110 | 1.5/110 |
| Digestion time (hrs)/°C. | 1.5/110 | 1.5/110 | 1.5/110 | 1.5/110 | 1.5/110 | 1.5/110 | 1.5/110 | 2.0110 | 1.5/110 |
| Vacuum stripping (hrs)/°C. | 2.0/110 | 2.0/110 | 2.0/110 | 2.0/110 | 2.0/110 | 2.0/110 | 2.0/110 | 1.5/110 | 2.0/110 |
| Total cycle time (hrs) | 8.0 | 8.0 | 8.0 | 8.0 | 10.0 | 8.0 | 7.0 | 8.0 | 7.0 |
| Final product weight (lbs) | 22.45 | 22.9 | 78.6 | 22.6 | 68.3 | 13.2 | 34.2 | 28.0 | 16.0 |

TABLE III-continued

| | Sucrose-Amino Polyols | | | | | | | | |
|---|---|---|---|---|---|---|---|---|---|
| | A | B | C | D | E | F | G | H | I |
| Polyol analysis | | | | | | | | | |
| Hydroxyl number (mg KOH/g) | 522 | 517 | 534 | 483 | 537 | 534 | 508 | 503 | 525 |
| Total amine (meq/g) | 0.87 | 0.84 | 1.27 | 0.52 | 0.95 | 1.22 | 0.35 | 0.22 | 0.32 |
| Viscosity, Brookfield (25° C.), cps | 12,000 | 8,800 | 8,710 | 16,680 | 28,360 | 41,700 | 3,570 | 9,240 | 7,460 |
| Water, wt. % | 0.11 | 0.06 | 0.09 | 0.03 | 0.03 | 0.01 | 0.086 | 0.01 | 0.01 |
| Color, Gardner | 12–13 | 11–12 | 3–4 | 10–11 | 10 | 13–14 | <1 | 2–3 | <1 |
| pH (isopropanol:$H_2O$:10:1) | 10.0 | 10.1 | 10.8 | 11.6 | 10.5 | 12.0 | 11.1 | 11.2 | 11.4 |
| Percent sucrose in polyol | 25.3 | 24.8 | 21.7 | 25.2 | 29.3 | 25.7 | 20.0 | 24.4 | 21.4 |
| Molecular weight (no. avg.) $M_n$ | — | 493 | — | 592 | — | 670 | — | — | — |
| Approximate hydroxyl functionality | — | 4.55 | — | 5.1 | — | 6.8 | — | — | — |

[1]EO was added with PO.
[2]20% added with EO.

TABLE IV

| | Rigid Foams from Sucrose Urea Polyols | | | | | | |
|---|---|---|---|---|---|---|---|
| | 1 | 2 | 3 | 4 | 5 | 6 | 7 |
| Formulation, pbw | | | | | | | |
| Polyol B | 37.6 | — | — | — | — | — | — |
| Polyol A | — | 37.2 | 37.2 | — | — | — | — |
| THANOL ® R-480[1] | — | — | — | 36.6 | — | — | — |
| Polyol C | — | — | — | — | 36.7 | — | — |
| Polyol G | — | — | — | — | — | 37.9 | — |
| Polyol H | — | — | — | — | — | — | 38.0 |
| Catalyst 4815-42[2] (DMAPU) | — | — | 0.5 | 0.5 | — | — | — |
| Catalyst DABCO ® LV-33[3] | 0.5 | 0.5 | — | — | 0.5 | — | — |
| Catalyst THANCAT ® TD-33 | — | — | — | — | — | 0.5 | 0.5 |
| Silicone DC-193 | 0.5 | 0.5 | 0.5 | 0.5 | 0.5 | 0.5 | 0.5 |
| Blowing agent R-11B[4] | 13.0 | 13.0 | 13.0 | 13.0 | 13.0 | 13.0 | 13.0 |
| THANATE ® P-270[5] | 48.4 | 48.8 | — | — | — | — | — |
| MONDUR ® MR[6] | — | — | 48.2 | 49.4 | 49.3 | 48.1 | 48.0 |
| Isocyanate index | 1.05 | 1.05 | 1.05 | 1.05 | 1.05 | 1.05 | 1.05 |
| Reaction rates | | | | | | | |
| Mixing time, sec | 15 | 15 | 15 | 15 | 15 | 12 | 12 |
| Cream time, sec | 33 | 34. | 30 | 32 | 30 | 17 | 20 |
| Tack free time, sec | 105 | 110 | 120 | 125 | 105 | 42 | 50 |
| Rise time, sec | 155 | 160 | 200 | 200 | 145 | 70 | 80 |
| Initial surface friability | Very slight | Very slight | Yes | Very slight | Very slight | None | Yes |
| Foam appearance | | | | Good | | | |
| Physical properties | | | | | | | |
| Density (lb/ft$^3$) | 2.17 | 2.16 | 2.07 | 2.06 | 2.21 | 1.97 | 2.04 |
| K-factor | 0.116 | 0.121 | 0.132 | 0.132 | 0.119 | 0.118 | 0.183 |
| Compress. strength, psi | | | | | | | |
| with rise | 47.87 | 47.53 | 36.43 | 30.47 | 43.75 | 38.26 | 36.60 |
| without rise | 17.42 | 17.09 | 14.61 | 15.84 | 16.58 | 16.10 | 21.60 |
| Heat distortion (°C.) | 177 | 181 | 190 | 191 | 190 | 151 | 172 |
| % Closed cells | 94.34 | 93.85 | 91.15 | 89.0 | 93.23 | 90.62 | 90.37 |
| Friability, wt. % loss | 5.5 | 8.6 | 14.7 | 17.6 | 8.3 | 3.8 | 5.2 |
| Dimensional stability | | | | | | | |
| 158° F., 100% RH, 1 week | | | | | | | |
| % volume change | +4.2 | +4.1 | +4.6 | +5.6 | +2.5 | +12.0 | +6.9 |
| % weight change | −0.7 | −0.7 | −2.2 | −2.8 | −1.1 | −0.5 | −1.5 |
| 180° F., dry, 1 week | | | | | | | |
| % volume change | +3.7 | +2.9 | +4.6 | +4.7 | +3.4 | +3.0 | +3.3 |
| % weight change | −0.7 | −0.5 | −1.1 | −1.6 | −1.1 | −0.8 | −1.7 |
| −20° F., dry, 1 week | | | | | | | |
| % volume change | −2.3 | −1.7 | −2.7 | −3.2 | −2.5 | −2.6 | −2.0 |
| % weight change | +1.0 | +0.8 | 0 | +0.1 | +0.1 | +0.9 | +2.9 |

[1]Sucrose amino polyol from Texaco Chemical Co.
[2]Bis(dimethylaminoproply)urea.
[3]Tertiary amine catalyst from Air Products and Chemicals, Inc.
[4]Du Pont, FCCl$_3$
[5]Texaco Chemical Co. polymeric isocyanate.
[6]Mobay polymeric isocyanate.

We claim:

1. A polyol having reduced color prepared by a process comprising reacting a polyhydric initiator or mixtures thereof with one or more alkylene oxides in the presence of a catalytically effective amount of urea such that the mole ratio of urea to the polyhydric initiator is from about 0.1:1 to about 10:1.

2. The polyol having reduced color prepared by a process comprising reacting a polyhydric initiator or mixtures thereof with one or more alkylene oxides in the presence of a catalytically effective amount of urea such that the mole ratio of urea to the polyhydric initiator is from about 0.1:1 to about 10:1, wherein the polyhydric initiator is selected from the group consisting of ethylene glycol, polyethylene glycol, propylene glycol, polypropylene glycol, glycerine, sorbitol, trimethylolpropane, sucrose, alpha-methylglucoside and pentaerythritol.

3. A polyol having reduced color prepared by a process comprising reacting aqueous sucrose with one or more alkylene oxides in the presence of a catalytically effective amount of urea such that the mole ratio of urea to sucrose is from about 0.1:1 to about 10:1.

4. The polyol of claim 3 wherein the urea is present in an amount such that the mole ratio of urea to sucrose is from about 0.2:1 to about 2:1.

5. The polyol of claim 3 wherein the mole ratio of alkylene oxide to sucrose is from about 8:1 to about 20:1.

6. The polyol of claim 3 wherein the sucrose is reacted with an alkylene oxide selected from the group consisting of ethylene oxide, propylene oxide and butylene oxide.

7. The polyol of claim 3 wherein the sucrose is reacted with one or more alkylene oxides in the presence of a catalytically effective amount of a tertiary amine co-catalyst.

8. A polyol having reduced color prepared by a process comprising reacting aqueous sucrose with one or more alkylene oxides containing from 2 to 4 carbon atoms, wherein the mole ratio of alkylene oxide to sucrose is from about 8:1 to about 20:1, in the presence of an amount of urea such that the mole ratio to sucrose is from about 0.2:1 to about 2:1.

9. The polyol of claim 8 wherein the sucrose is reacted with one or more alkylene oxides in the presence of a catalytically effective amount of a tertiary amine co-catalyst.

10. A process for producing a polyol having reduced color consisting essentially of reacting a polyhydric initiator or mixtures thereof with one or more alkylene oxides in the presence of a catalytically effective amount of urea such that the mole ratio of urea to the polyhydric initiator is from about 0.1:1 to about 10:1.

11. The process for producing a polyol having reduced color consisting essentially of reacting a polyhydric initiator or mixtures thereof with one or more alkylene oxides in the presence of a catalytically effective amount of urea such that the mole ratio of urea to the polyhydric initiator is from about 0.1:1 to about 10:1, wherein the polyhydric initiator is selected from the group consisting of ethylene glycol, polyethylene glycol, propylene glycol, polypropylene glycol, glycerine, sorbitol, trimethylolpropane, sucrose, alpha-methylglucoside and pentaerythritol.

12. A process for producing a polyol having reduced color comprising reacting aqueous sucrose with one or more alkylene oxides in the presence of a catalytically effective amount of urea such that the mole ratio of urea to the polyhydric initiator is from about 0.1:1 to about 10:1, in the absence of a subsequent alkoxylation with an added catalyst.

13. The process of claim 12 wherein the urea is present in an amount such that the mole ratio of urea to sucrose is from about 0.2:1 to about 2:1.

14. The process of claim 12 wherein the mole ratio of alkylene oxide to sucrose is from about 8:1 to about 20:1.

15. The process of claim 12 wherein the sucrose is reacted with an alkylene oxide selected from the group consisting of ethylene oxide, propylene oxide and butylene oxide.

16. The process of claim 12 wherein the sucrose is reacted with one or more alkylene oxide in the presence of a catalytically effective amount of a tertiary amine co-catalyst.

17. A process for producing a polyol having reduced color by reacting aqueous sucrose with one or more alkylene oxides containing from 2 to 4 carbon atoms, wherein the mole ratio of alkylene oxide to sucrose is from about 8:1 to about 20:1, in the presence of an amount of urea such that the mole ratio of urea to sucrose is from about 0.2:1 to about 2:1, in the absence of a subsequent alkoxylation with an added catalyst.

18. The process of claim 17 wherein the sucrose is additionally reacted with one or more alkylene oxides in the presence of a catalytically effective amount of a tertiary amine co-catalyst.

19. A process for producing a polyol having reduced color comprising reacting a polyhydric initiator or mixtures thereof with one or more alkylene oxides where the only catalyst employed is urea in a catalytic effective amount.

20. The process of claim 19 wherein the polyhydric initiator is selected from the group consisting of ethylene glycol, polyethylene glycol, propylene glycol, polypropylene glycol, glycerine, sorbitol, trimethylolpropane, sucrose, alpha-methylglucoside and pentaerythritol.

* * * * *